United States Patent

Moss

[11] 4,053,984
[45] Oct. 18, 1977

[54] MOUTH PROP

[76] Inventor: Dan E. Moss, 247 Ridge Road, Cedar City, Utah 84720

[21] Appl. No.: 711,825

[22] Filed: Aug. 5, 1976

[51] Int. Cl.$^2$ .................................................. A61C 7/00
[52] U.S. Cl. ........................................... 32/33; 128/12; 32/34
[58] Field of Search ........................ 32/33, 34; 128/275, 128/12, 13, 14, 15

[56] References Cited

U.S. PATENT DOCUMENTS

| 1,401,646 | 12/1921 | Ronn | 32/33 |
| 2,859,519 | 11/1958 | Cohn | 32/33 |
| 3,455,024 | 7/1969 | Gelarie | 32/33 |

Primary Examiner—Robert Peshock

[57] ABSTRACT

A removable dental appliance is disclosed which props open the mouth for dental work while maintaining a dry and wide field of operation. The appliance includes a flexible tubular frame having upper and lower U-shaped sections which are adapted to fit into the patient's mouth outside of the upper and lower dental arches in surface contact with the cheeks. Cheek deflectors are removably secured between upper and lower U-shaped sections of the frame to force the patient's cheeks outward to prevent occlusion of the field of operation. The cheek deflectors are constructed from a flexible material which is curved generally outward to a contour approximating the cheek surface of the mouth. A tongue deflector is secured to the front of the bottom U-shaped section of the tubular support frame. The frame is provided with a plurality of orifices which permit the removal of saliva from the mouth when a vacuum source is applied to a saliva ejector which is coupled to the tubular frame. Upper and lower lip deflectors are attached to the front of the upper and lower portions of the tubular frame.

10 Claims, 3 Drawing Figures

MOUTH PROP

BACKGROUND OF THE INVENTION

1. Field of the Invention

The invention relates to dental appliances which are used for propping open the mouth to permit the dentist to have a wide and dry field of operation.

2. Description of the Prior Art

In the past, various appliances have been used to isolate or open parts of the mouth to facilitate the performing of dental services. Bite blocks and expansion forceps have been used to hold the patient's jaws open. These devices do not have any provision for protecting the soft tissues of the mouth from injury caused by the patient biting down on them. Nor do they have any provision for saliva removal. Moreover, unlike the present invention, they do not have a flexible frame to which are attached cheek deflectors which displace the cheeks outward when the patient bites down upon the flexible frame. Another common applicance used for isolating parts of the mouth is the rubber dam which consists of a flexible piece of material having holes disposed therein to permit placement down over the teeth into surface contact with the gums so that the teeth protrude through the holes in the rubber dam. Unlike the present invention, the rubber dam does not have a flexible frame having cheek and tongue deflectors attached thereto and the provision for saliva removed. Another appliance is a mouth prop sold by Parkell. This device consists of an oval shaped frame having lip deflectors attached thereto. It does not have provision for saliva ejection or tongue deflection. Moreover, it may only be used to isolate the anterior teeth.

U.S. Pats. No. 24,693, and Nos. 1,868,653, 2,587,008, 2,937,445, 3,078,578 and 3,772,790 disclose dental appliances which are used to facilitate the performance of dental work. None of these appliances disclose a flexible support frame having cheek deflectors which force the patients's cheeks outward away from the field of operation upon compression of the flexible frame by closing of the patient's jaws.

U.S. Pat. No. 3,396,468 discloses a dental appliance having a flexible support frame having a pair of U-shaped frame members which are respectively disposed inside and outside of one half of the upper and lower dental arches. The support frame has provision for the attachment of a rubber dam to isolate the dental arch from the rest of the mouth. A vacuum source may be attached to the lower part of the tubular support frame for drawing saliva inside the tubular frame through a plurality of holes which are disposed in the frame. This appliance differs substantially from the present invention in that it may only be used to isolate one half of the patient's mouth and that it does not have provision for a cheek deflector to force the patient's cheek outward away from the dental field of operation upon closing of the patient's jaws.

SUMMARY OF THE INVENTION

The disadvantages and limitations of the prior art dental appliances are obviated by the present invention which permits the dentist to have a wide and dry field of operation. The invention has at least the following advantages: The mouth prop is readily usable in different sized mouths and is cold sterilizable; it provides a dryer field of operation than is presently obtainable from bite blocks, saliva ejectors, cotton rolls or separate entity adaptions; it is more acceptable to the patient and dentist than the commonly used rubber dam; it does not require application to a specific area as is the case with the rubber dam; it opens the whole mouth to facilitate the performing of dental services; and it eliminates the requirement for the application of a plurality of appliances to achieve a wide field of operation, saliva ejection and a dry field of operation.

The invention includes a flexible support frame which has upper and lower U-shaped parts which are adapted to fit into the patient's mouth outside of the dental arches into surface contact with the patient's cheeks; first and second cheek deflectors which are respectively removably secured between the upper and lower U-shaped parts of the flexible support frame, the outer surface of the cheek deflectors being generally curved to a contour approximating the cheek surface of the mouth to force the patient's cheeks outward upon compression of the support frame by the patient's jaws; a tongue deflector which is removably secured to the front of the lower U-shaped part of the support frame to depress the tongue down into the mouth cavity when the flexible frame is inserted into the mouth; a plurality of holes which are disposed in the support frame to permit removal of saliva from the mouth cavity upon application of a vacuum source to a saliva ejector which is disposed external to the portion of the appliance which is adapted to be inserted into the mouth; and upper and lower lip deflectors which are respectively removably secured to the front portion of the upper and lower U-shaped parts of the flexible support frame to force the lips away from the mouth opening.

DETAILED DESCRIPTION OF THE INVENTION

Figure 1:
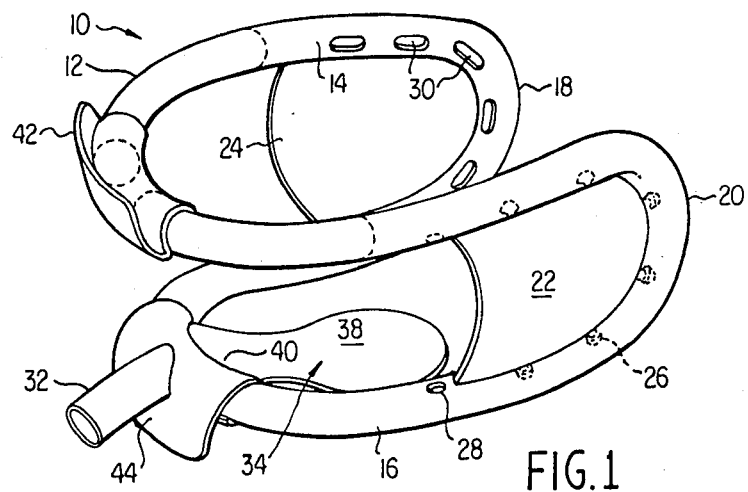
FIG. 1 is a three quarter perspective view of a dental appliance constructed according to the present invention.
Figure 2:
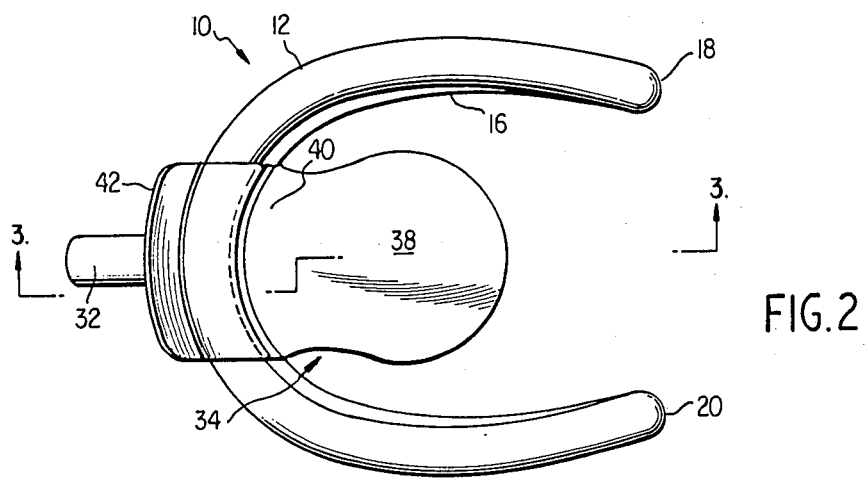
FIG. 2 is a top view of a dental appliance constructed according to the present invention.
Figure 3:
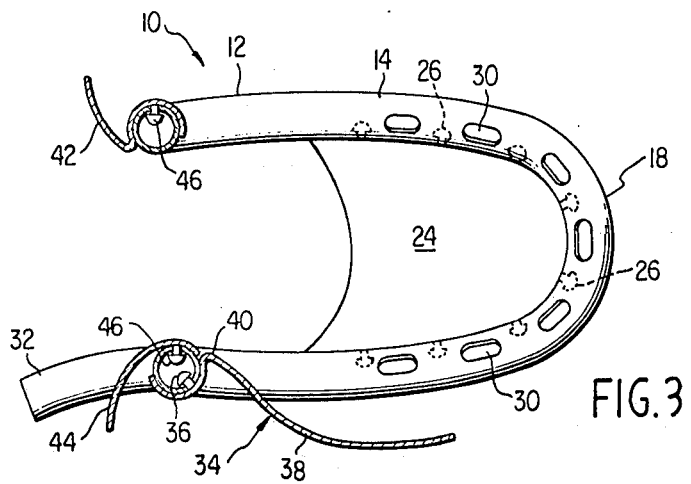
FIG. 3 is a sectional view of a dental appliance constructed according to the present invention.

FIGS. 1 through 3 respectively illustrate perspective, top and sectional views of a dental appliance 10 constructed according to the present invention. The tubular support frame 12 is comprised of an upper U-shaped section 14 and a lower U-shaped section 16 which are joined together by curved bights 18 and 20. The upper and lower U-shaped sections 14 and 16 and the bights 18 and 20 of the frame 12 comprise a support means. A pair of cheek deflectors 22 and 24 respectively are removably secured between the upper and lower U-shaped sections 14 and 16 of the tubular support frame 12 by fasteners 26 which fit into apertures 28 provided in the tubular support frame. The cheek deflectors 22 and 24 are curved outwardly away from the support frame 12 in a contour which generally approximates the cheek surface of the mouth. The cheek deflectors 22 and 24 are constructed from a pliable material which bends outwardly away from the tubular support frame 12 upon the inward bending of the bights 18 and 20 caused by compression of the patient'jaws. A plurality of apertures 30 are disposed in the support frame 12 to facilitate removal of saliva from the mouth area. A saliva ejector 32 is attached to the front center of the U-shaped section 16 of the support frame 12. The saliva ejector 32 comprises a cylindrical tube which is coupled to the interior tubular section of the support frame 12 so that saliva may be drawn in through the apertures 30 and out of the saliva ejector 32 upon the application of a suitable source of vacuum. A tongue deflector 34 is removably secured to the front of the U-shaped section 16 of the support frame 12 by means of a fastener 36 which fits in an aperture (not shown) in the front of the bottom U-shaped section 16. The tongue deflector 34 includes a generally elongated section 38 which is shaped to contact a large portion of a patient's tongue when the appliance 10 is disposed in the mouth. The tongue deflector 34 also includes a downwardly curved section 40 which is disposed adjacent to the point of attachment of the tongue deflector to the lower U-shaped section 16 of the support frame 12. The downwardly curved section 40 of the tongue deflector 34 should be sufficiently resilient to depress the patient's tongue downward into the mouth cavity upon insertion of the support frame into the patient's mouth. Upper and lower lip deflectors 42 and 44 respectively are removably secured to the front of the upper and lower U-shaped portions 14 and 16 of the support frame 12 by means of fasteners 46 which fit into apertures. The lip deflectors 42 and 44 are manufactured from a resilient but pliable material which is gently curved to a contour to force the patient's lips away from the mouth opening upon insertion into the mouth.

The front of the upper U-shaped section 14 of the frame 12 preferably has a solid cross section since it is not necessary to aspirate saliva from the top front portion. In the front portion of the solid cross section, a horizontally disposed slot, (not shown) may be provided for movably receiving fastener 46 to permit lateral adjustment of the position lip deflector 42 with respect to section 14.

The mouth prop 10 should be sufficiently resilient to support the patient's tongue, cheeks and jaws but sufficiently pliant to be deformed by conscious movement of the patient. The resiliency of bights 18 and 20 should hold the patient's jaws open sufficiently to give the dentist a wide field of operation within the patient's mouth.

The use of an appliance constructed according to the present invention is summarized as follows. The appliance 10 is inserted into the patient's mouth so that the upper and lower U-shaped portions 14 and 16 are disposed outside of the patient's upper and lower dental arches. The cheek deflectors 22 and 24 are secured in one of at least two longitudinal positions with respect to sections 14 and 16 of the support frame to force the patients's cheeks away from the field of operation within the patient's mouth. The closure of the patient's jaws forces the cheek deflectors 22 and 24 to curve further outward to extend the dental field of operation away from the dental arches. Upon insertion of the mouth prop into the mouth, the tongue deflector 34 forces the patient's tongue downward into the bottom portion of the mouth to create a field of operation unrestricted by the tongue. Lip deflectors 44 and 46 force the patient's lips away from the opening of the mouth to permit the dentist to have access to the field of operation inside the patient'mouth. Upon attachment of a source of vacuum to saliva ejector 32 after insertion of the dental mouth prop into the patient's mouth, saliva is drawn from the patient's mouth through the apertures 30 contained in the support frame 12 to facilitate the maintenance of a dry field of operation within the patient's mouth.

It is preferable that the present invention should be constructed from a pliable plastic which may be suitably sterilized and used in the oral environment.

While the invention has been described in terms of preferred embodimment, it should be apparent to those persons skilled in the art that numerous modifications may be made thereto without departing from the spirit and scope of the invention. Accordingly, it is intended that all such modifications fall within the scope of the appended claims.

What I claim is:

1. A dental mouth prop comprising:
 a. a support having an upper U-shaped section with first and second ends, a lower U-shaped section with first and second ends, a first curved connecting section joining the first end of said upper U-shaped section to the first end of said lower U-shaped section, a second curved connecting section joining the second end of said upper U-shaped section to the second end of said lower U-shaped section;
 b. first and second cheek deflectors respectively secured to different sides of said upper and lower U-shaped sections, said cheek deflectors being curved generally to a contour approximating the cheek surface of the mouth, said cheek deflectors holding the patient's cheeks away from the dental arches when said mouth prop is inserted into the patient's mouth.

2. The mouth prop of claim 1 further comprising:
 a tongue deflector secured to said support at the front of said lower U-shaped section, said tongue deflector holding the patient's tongue in the lower portion of the patient's mouth when said mouth prop is inserted into the patients's mouth.

3. The mouth prop of claim 1 wherein:
 a. said support is constructed from a flexible tubular member;
 b. said tubular member has a plurality of orifices which drain saliva from the patient's mouth when said mouth prop is inserted into the patient's mouth; and further comprising
 c. a section of tubing coupled to said tubular member for draining the saliva within said tubular member.

4. The mouth prop of claim 1 wherein:
 a. said upper and lower U-shaped sections are constructed from flexible tubing; and
 b. said connecting sections comprise flexible tubular bights.

5. The mouth prop of claim 1 further comprising:
 upper and lower lip deflectors respectively secured to the front of said upper and lower U-shaped sections of said support, said lip deflectors engaging the upper and lower lips of the patient when said mouth prop is inserted into the patient'mouth.

6. The mouth prop of claim 1 wherein:
 said cheek deflectors are formed from a flexible material which bends away from said upper and lower U-shaped sections upon inward bending of said connecting sections during closing of the patient'-mouth.

7. The mouth prop of claim 5 wherein:
 a. said upper and lower lip deflectors are removably secured to apertures in the front of said U-shaped sections by fasteners; and further comprising
 b. a tongue deflector secured to said support at the front of said lower U-shaped section, said tongue deflector holding the patient's tongue in the lower portion of the patient's mouth when said mouth prop is inserted into the patient's mouth; and wherein c. said tongue deflector is removably secured to an aperture in said lower U-shaped section by a fastener.

8. The mouth prop of claim 6 further comprising:
a. a plurality of apertures disposed along the sides of said upper and lower U-shaped sections; and
b. a plurality of fasteners attached to said cheek deflectors for removably securing said cheek deflectors to the sides of said U-shaped sections by insertion of said fasteners into said apertures, said cheek deflectors being removably securable to said upper and lower U-shaped sections in more than one position disposed along the sides of said U-shaped sections.

9. A dental mouth prop comprising:
a. a support constructed from a flexible tubular member having an upper U-shaped section with first and second ends, a lower U-shaped section with first and second ends, a first curved connecting section joining the first end of said upper U-shaped section to the first end of said lower U-shaped section, a second curved connecting section joining the second end of upper U-shaped section to the second end of said lower U-shaped section;
b. first and second cheek deflectors respectively secured to different sides of said upper and lower U-shaped sections, said cheek deflectors being curved generally to a contour approximating the cheek surface of the mouth, said cheek deflectors holding the patient's cheeks away from the dental arches when said mouth prop is inserted into the patient's mouth;
c. a tongue deflector secured to said support at the front of said lower U-shaped section, said tongue deflector holding the patients's tongue in the lower portion of the patient's mouth when said mouth prop is inserted into the patient's mouth;
d. upper and lower lip deflectors respectively secured to the front of said upper and lower U-shaped sections of said support, said lip deflectors engaging the upper and lower lips of the patient's mouth when said mouth prop is inserted into the patient's mouth;
e. said tubular member having a plurality of orifices which drain saliva from the patient's mouth when said mouth prop is inserted into the patient's mouth; and
f. a section of tubing coupled to said tubular member for draining the saliva within said tubular member.

10. The mouth prop of claim 9 wherein:
a. said cheek deflectors are formed from a flexible material which bends away from said upper and lower U-shaped sections upon inward bending of said connecting sections during closing of the patient's mouth;
b. a plurality of apertures are disposed along the sides of said upper and lower U-shaped sections;
c. a plurality of fasteners are attached to said cheek deflectors for removably securing said cheek deflectors to the sides of said U-shaped sections by insertion of said fasteners into said apertures, said cheek deflectors being removably securable to said upper and lower U-shaped sections in more than one position disposed along the sides of said U-shaped sections;
d. said upper and lower lip deflectors are removably secured to apertures in the front of said U-shaped sections by fasteners; and
e. said tongue deflector is removably secured to an aperture in said lower U-shaped section by a fastener.

* * * * *